US007991730B2

(12) United States Patent
Wagner et al.

(10) Patent No.: US 7,991,730 B2
(45) Date of Patent: Aug. 2, 2011

(54) METHODS FOR SIMILARITY SEARCHING OF CHEMICAL REACTIONS

(75) Inventors: Alain Wagner, Strasbourg (FR); Frank Hoonakker, Bischoffsheim (FR); Alexandre Varnek, Strasbourg (FR)

(73) Assignees: Novalyst Discovery, Illkirch Graffenstaden (FR); Universite Louis Pasteur, Strasbourg (FR)

(*) Notice: Subject to any disclaimer, the term of this patent is extended or adjusted under 35 U.S.C. 154(b) by 717 days.

(21) Appl. No.: 11/779,255

(22) Filed: Jul. 17, 2007

(65) Prior Publication Data
US 2009/0024575 A1    Jan. 22, 2009

(51) Int. Cl.
G06F 17/30 (2006.01)
G06F 7/00 (2006.01)
G06F 19/00 (2006.01)

(52) U.S. Cl. ............ 707/104.1; 707/102; 707/101; 702/27

(58) Field of Classification Search .......... 707/104.1, 707/101, 102; 702/19–32; 703/11–12
See application file for complete search history.

(56) References Cited

U.S. PATENT DOCUMENTS

| | | | |
|---|---|---|---|
| 6,274,689 B1* | 8/2001 | Shaffer et al. | 526/336 |
| 6,508,988 B1* | 1/2003 | Van Dam et al. | 422/102 |
| 7,112,658 B2* | 9/2006 | Owyang | 530/350 |
| 2002/0013000 A1* | 1/2002 | Fagrell et al. | 436/50 |
| 2004/0173604 A1* | 9/2004 | Fagrell | 219/679 |

OTHER PUBLICATIONS

"Reaction fingerprint, Version 3.2.3," [online]. ChemAxon Ltd., webpage copyrighted 1999-2007 [retrieved on Jul. 21, 2009]. Retrieved from the Internet: <URL: http://web.archive.org/web/20070207133852/http://www.chemaxon.com/jchem/doc/user/RFp.html>.
International Search Report in PCT/IB2008/052851 having a mailing date of Apr. 20, 2009.
Hanser, Th., et al., "CGS: Condensed Graph of Synthesis, a New Computer Representation for Molecules, Reactions and Syntheses," American Institute of Physics Conference Proceedings No. 330, [online], (1995), 575-581.
Reaction fingerprint, Version 3.2.3, [online]. ChemAxon Ltd., webpage copyrighted 1999-2007 [retrieved on Jul. 21, 2009]. Retrieved from the Internet: <URL: http://web.archive.org/web/20070207133852/http://www.chemaxon.com/jchem/doc/user/RFp.html>.
Varnek, A., et al., "Substructural fragments: an universal language to encode reactions, molecular and supramolecular structures," *Journal of Computer-Aided Molecular Design*, (2005), 19, 693-703.
International Search Report in PCT/IB2008/052851 having a mailing date of Apr. 20, 2009.
Written Opinion of the International Searching Authority in PCT/IB2008/052851.
Grethe, G. and Moock, T., "Similarity Searching in REACCS. A New Tool for the Synthetic Chemist, " *Journal of Chemical Information and Computer Sciences*, 1990, vol. 30, pp. 511-520.
Willett, P., et al., "Chemical Similarity Searching," *Journal of Chemical Information and Computer Sciences*, 1998, vol. 38, pp. 983-996.

* cited by examiner

Primary Examiner — Kuen S Lu
(74) Attorney, Agent, or Firm — O'Brien Jones, PLLC

(57) ABSTRACT

A computer-based method for identifying at least one pair of similar chemical reactions between a plurality of reactions each related to preparation of at least one product from at least one reagent may include generating for each reaction a structural representation involving dynamic and conventional bonds and, based on the this structural representation, generating for each reaction a set of fragment descriptors of a predetermined length comprising the dynamical bonds and a corresponding descriptor vector. The method may further include calculating similarity indices between descriptor vectors of the plurality of reactions and comparing the similarity indices to identify at least one pair of similar reactions.

14 Claims, 15 Drawing Sheets

```
$RXN 2 1
$MOL 7  7  0  0  0  0  0  0  0999 V2000
    0.8250   -0.7145    0.0000 C   0  0  0  0  0  0  0  0  0  0  0  0
    1.2375   -0.0000    0.0000 C   0  0  0  0  0  0  0  0  0  0  0  0
    0.8250    0.7145    0.0000 C   0  0  0  0  0  0  0  0  0  0  0  0
    0.0000    0.7145    0.0000 C   0  0  0  0  0  0  0  0  0  0  0  0
   -0.4125   -0.0000    0.0000 C   0  0  0  0  0  0  0  0  0  0  0  0
    0.0000   -0.7145    0.0000 C   0  0  0  0  0  0  0  0  0  0  0  0
   -1.2375   -0.0000    0.0000 Br  0  0  0  0  0  0  0  0  0  0  0  0
  1  2  4  0     0
  2  3  4  0     0
  3  4  4  0     0
  4  5  4  0     0
  5  6  4  0     0
  6  1  4  0     0
  5  7  1  0     0
M  END
$MOL 6  5  0  0  0  0  0  0  0999 V2000
    1.0313    0.7145    0.0000 C   0  0  0  0  0  0  0  0  0  0  0  0
    0.2062    0.7145    0.0000 C   0  0  0  0  0  0  0  0  0  0  0  0
   -0.2062   -0.0000    0.0000 C   0  0  0  0  0  0  0  0  0  0  0  0
    0.2062   -0.7145    0.0000 O   0  0  0  0  0  0  0  0  0  0  0  0
   -1.0313   -0.0000    0.0000 O   0  0  0  0  0  0  0  0  0  0  0  0
    1.0313   -0.7145    0.0000 C   0  0  0  0  0  0  0  0  0  0  0  0
  1  2  2  0     0
  2  3  1  0     0
  3  4  1  0     0
  3  5  2  0     0
  4  6  1  0     0
M  END
$MOL 12 12  0  0  0  0  0  0  00999 V2000
    0.7145    0.0000    0.0000 C   0  0  0  0  0  0  0  0  0  0  0  0
    0.7145   -0.8250    0.0000 C   0  0  0  0  0  0  0  0  0  0  0  0
    1.4289   -1.2375    0.0000 C   0  0  0  0  0  0  0  0  0  0  0  0
    2.1434   -0.8250    0.0000 C   0  0  0  0  0  0  0  0  0  0  0  0
    2.1434    0.0000    0.0000 C   0  0  0  0  0  0  0  0  0  0  0  0
    1.4289    0.4125    0.0000 C   0  0  0  0  0  0  0  0  0  0  0  0
    0.0000    0.4125    0.0000 C   0  0  0  0  0  0  0  0  0  0  0  0
   -0.7145    0.0000    0.0000 C   0  0  0  0  0  0  0  0  0  0  0  0
   -1.4289    0.4125    0.0000 C   0  0  0  0  0  0  0  0  0  0  0  0
   -2.1434    0.0000    0.0000 O   0  0  0  0  0  0  0  0  0  0  0  0
   -1.4289    1.2375    0.0000 O   0  0  0  0  0  0  0  0  0  0  0  0
   -2.1434   -0.8250    0.0000 C   0  0  0  0  0  0  0  0  0  0  0  0
  1  2  4  0     0
  2  3  4  0     0
  3  4  4  0     0
  4  5  4  0     0
  5  6  4  0     0
  6  1  4  0     0
  1  7  1  0     0
  7  8  2  0     0
  8  9  1  0     0
  9 10  1  0     0
  9 11  2  0     0
 10 12  1  0     0
M  END
```

FIG. 6

```
13 13  0  0  0  0  0  0  0  0999  V2000
   0.7145   0.0000   0.0000 C   0  0  0  0  0  0  0  0  0  0  0  0
   0.7145  -0.8250   0.0000 C   0  0  0  0  0  0  0  0  0  0  0  0
   1.4289  -1.2375   0.0000 C   0  0  0  0  0  0  0  0  0  0  0  0
   2.1434  -0.8250   0.0000 C   0  0  0  0  0  0  0  0  0  0  0  0
   2.1434   0.0000   0.0000 C   0  0  0  0  0  0  0  0  0  0  0  0
   1.4289   0.4125   0.0000 C   0  0  0  0  0  0  0  0  0  0  0  0
   0.0000   0.4125   0.0000 C   0  0  0  0  0  0  0  0  0  0  0  0
  -0.7145   0.0000   0.0000 C   0  0  0  0  0  0  0  0  0  0  0  0
  -1.4289   0.4125   0.0000 C   0  0  0  0  0  0  0  0  0  0  0  0
  -2.1434   0.0000   0.0000 C   0  0  0  0  0  0  0  0  0  0  0  0
  -1.4289   1.2375   0.0000 O   0  0  0  0  0  0  0  0  0  0  0  0
  -2.1434  -0.8250   0.0000 C   0  0  0  0  0  0  0  0  0  0  0  0
  -1.2375  -0.00 00   0.0000 Br  0  0  0  0  0  0  0  0  0  0  0  0
  1  2  4  0  0  0  0
  2  3  4  0  0  0  0
  3  4  4  0  0  0  0
  4  5  4  0  0  0  0
  5  6  4  0  0  0  0
  6  1  4  0  0  0  0
  1  7  81 0  0  4  0
  7  8  2  0  0  0  0
  8  9  1  0  0  0  0
  9 10  1  0  0  0  0
  9 11  2  0  0  0  0
 10 12  1  0  0  0  0
 13  1  18 0  0  0  0
M  END
$$$$
```

Here these two bond type's code for dynamical bonds. 81 mean that bond is created and 18 mean that bond is break.

FIG. 7

I(AB,2-6)
1 28
Set of Fragments.
1. C=C1C*C*C*C
2. C*C1C
3. Br5C1C=C-C=O
4. C=C1C*C*C
5. C*C*C*C*C1C
6. C-C=C1C*C
7. C1C=C-C=O
8. C*C1C=C-C-O
9. C1C
10. Br5C
11. C-O-C-C=C1C
12. C*C*C1C
13. Br5C*C*C
14. C-C=C1C
15. Br5C5Br
16. C=C1C
17. Br5C1C=C-C-O
18. Br5C*C
19. C-C=C1C*C*C
20. Br5C1C=C-C
21. Br5C1C
22. Br5C*C*C*C*C
23. C*C1C=C-C=O
24. C1C=C-C-O
25. C*C*C*C1C
26. Br5C*C*C*C
27. C=C1C*C
28. Br5C1C=C

FIG. 8

MATRIX: Compound (Line) Fragment_Number:Number_of_Fragment.
1 2 2 2 3 2 4 2 5 2 6 2 7 1 8 2 9 1 10 2 11 1 12 2 13 4 14 1 15 1 16 1 17 2 18 4 19 2 20 2 21 2 22 4 23 2 24 1
25 2 26 4 27 2 28 2

MATRIX: Compound (Line) Fragment_Number:Number_of_Fragment.
1 1 2 1 3 1 4 1 5 1 6 1 7 1 8 1 9 1 10 1 11 1 12 1 13 1 14 1 15 1 16 1 17 1 18 1 19 1 20 1 21 1 22 1 23 1 24 1
25 1 26 1 27 1 28 1

I(AB,2-6)
1-43
Set of Fragments.
1. C=C1C*N*C
2. C-C=C1C*N
3. Br5C1C
4. C1C*N
5. C1C=C-C-O
6. C=C1C*N*C*C
7. C1C=C*N
8. Br5C*C*N*C
9. C*C1C=C-C-O
10. C*C*N*C*C1C
11. Br5C*N*C*C*N
12. N*C1C=C-C=O
13. C1C
14. Br5C1C=C
15. C=C1C*C*N
16. Br5C1C=C-C-O
17. C1C=C-C=O
18. Br5C5Br
19. C-C=C1C*N*C
20. C=C1C*C
21. C*C1C
22. C1C*N*C*C*N
23. Br5C*C*N*C*C
24. Br5C*N*C
25. C=C1C*N
26. C=C1C
27. Br5C*C
28. N*C1C=C-C-O
29. C=C1C*C*N*C
30. Br5C1C=C-C
31. C*N*C1C
32. Br5C1C=C-C-O
33. Br5C*N*C*C
34. Br5C*N
35. C*C*N*C1C
36. C-C=C1C*C*N
37. C-C=C1C
38. C*C1C=C-C-O
39. C*N*C*C1C
40. C-C=C1C*C
41. Br5C*C*N
42. C-O-C-C-C1C
43. Br5C

FIG. 14

MATRIX: Compound(Line) : Fragment_Number Number_of_Fragment.
1 1 2 1 3 2 4 1 5 1 6 1 7 1 8 2 9 1 10 1 11 2 12 1 13 1 14 2 15 1 16 2 17 1 18 1 19 1 20 1 21 1 22 1 23 2 24 2 25 1 26 1 27 2 28 1 29 1 30 2 31
1 32 2 33 2 34 2 35 1 36 1 37 1 38 1 39 1 40 1 41 2 42 1 43 2

FIG. 15

| | |
|---|---|
| 1 | single bond |
| 2 | double bond |
| 3 | triple bond |
| 4 | aromatic bond |
| 81 | made single bond |
| 82 | made double bond |
| 83 | made triple bond |
| 84 | made aromatic bond |
| 12 | made double bond from single bond |
| 13 | made triple bond from single bond |
| 14 | made romatic bond from single bond |
| 18 | broken single bond |
| 21 | broken double bond to single bond |
| 23 | made triple bond from double bond |
| 24 | made aromatic bond from double bond |
| 28 | broken double bond |
| 31 | broken double bond to single bond |
| 32 | broken triple bond to double bond |
| 34 | made aromatic bond from triple bond |
| 38 | broken triple bond |

METHODS FOR SIMILARITY SEARCHING OF CHEMICAL REACTIONS

FIELD

The present invention relates to a method for identifying at least one pair of similar chemical reactions in order to search, for example, for reaction conditions and/or to investigate large reaction databases. The invention also relates to a method for chemical testing of substances.

BACKGROUND

Computational chemistry is used by chemists to accelerate molecule design and optimization.

For a given target reaction, a substructural search in a reaction database (SciFinder®, Beilstein® or any other) may help a chemist to find approximately the closest reaction. Structural similarity may suggest similar conditions.

In a substructural search, the query represents a sub-graph of the target chemical reaction. Therefore, the chemist should know the database in order to create the appropriate query leading to the pertinent responses. In many cases, the search provides either too many results because the query is not selective enough or no results because the query is too selective.

A similarity search, which is in relatively wide use for individual molecules, is very rarely applied to chemical reactions because of two main problems. The first problem is related to several molecules being involved in a reaction. The second problem lies in the difficulties in taking into account distinctions between reactants and products.

The article *Chemical Similarity Searching* in J. Chem. Ing. Comput; Sci 1998, 38, 983-996, by P. Willett, which is hereby incorporated by reference in its entirety, reviews the use of similarity searching in chemical databases of individual molecules.

In classical similarity searching, a query may involve the specification of an entire molecule via a set of descriptors which are compared with a corresponding set of descriptors for each molecule in a database.

The procedure is based on the calculation of indices of similarity between the target molecule and each molecule of the database. Results may be represented by a ranked list in which the most similar structures to the target molecule are at the top of the list.

The article, *Similarity Searching in REACCS A New Tool for the Synthetic Chemist* in J. Chem. Inf. Comput. Sci. 1990, 30, 511-520, by Gretge and Moock, reviews the use of REACCS (Reaction System of the MDL company for similarity searching). REACCS determines a degree of similarity between two molecules or two reactions by calculating an amount of overlap between fragment structures.

More recently, the company ChemAxon has developed a method to calculate similarity between reactions based on fragment structures of reactants and products.

It may be desirable to provide a method for similarity searching between chemical reactions that is user friendly, efficient and easy to implement. It also may be desirable to provide a method for similarity searching between chemical reactions that may help in many areas of chemistry, like reaction searching, reagents and reaction condition selection, design of reactional pathway, exploiting laboratory notebook or piloting automated synthesis platform.

SUMMARY

According to an exemplary aspect, the present invention may provide a computer implemented method for assessment of similarity of two chemical reactions.

An exemplary embodiment of the invention may provide a method for identifying at least one pair of similar chemical reactions between a plurality of reactions each related to the preparation of at least one product from at least one reagent, the method may comprise generating for each reaction a structural representation involving both conventional and dynamic bonds, and, based on this structural representation, generating for each reaction a set of fragment descriptors of a predetermined length comprising the dynamical bonds and a corresponding descriptor vector. The method may further include calculating similarity indices between descriptor vectors, and comparing the similarity indices to identify at least one pair of similar reactions.

The method may also comprise providing the user reaction information related to the at least one similar reaction pair.

This method may also comprise classifying reactions of a database according to the calculated similarity indices. In such case, no query may be needed. The database may be any publicly accessible or private database. The database may comprise a laboratory notebook.

Dynamical bonds are bonds that are created, broken or modified during the chemical reaction. Conventional bonds are bonds that, remain unchanged during the chemical reaction.

The similarity indices may be calculated by any method that allows calculation of distances between chemical objects using fragment descriptors.

The similarity indices may be computed as a distance between two descriptor vectors and the metric may be selected in the group consisting of Hamming distance, Euclidean distance, Soergel distance, Tanimoto coefficients, Dice coefficients or Cosine Coefficients. Other metrics may be used.

A cut-off value and/or a number of responses may be used to limit the number of responses retrieved by the method. The cut-off value may be inputted by a user and/or set by default.

Another exemplary embodiment of the present invention may include a method comprising enabling input of a query reaction, generating for the query reaction a structural representation involving dynamic and conventional bonds. The method may further include, generating a query descriptor vector based on the structural representation and calculating similarity indices between the query descriptor vector and candidate descriptor vectors generated from a database. The method may also include comparing the similarity indices to identify at least one reaction similar to the query reaction.

A candidate descriptor vector may be any descriptor vector corresponding to one reaction in the database. The query descriptor vector may be generated the same way as each candidate descriptor vector.

In exemplary embodiments, the invention provides a method based on a Condensed Graph of Reaction (CGR) approach. CGR is a condensed representation of a reaction using a completely connected and non-oriented graph. The edges represent all the bonds of the reaction and the nodes represent the atoms in the reaction. The CGR may look like a compound with the addition of the dynamical bonds. The formal valence of atoms does not need to be respected when drawing the dynamical bonds.

Each CGR may be associated with a CGR vector having for attributes occurrences of fragment descriptors in accordance to the CGR.

The method may comprise computing similarity indices between reactions using CGR vectors and sorting similarity indices to identify at least one chemical reaction in the database that is most similar to the query.

The method may comprise prompting a user to select a cut-off value that allows sorting of the most similar reactions.

The identification of a similar reaction may be used, for example, for providing reaction information related to this reaction. The reaction information may comprise reactional condition information, i.e. parameters that allow the chemical reaction. It may comprise at least one of temperature conditions, pressure conditions, yield, catalyst, solvent, additive, and identifiers.

The invention may be useful to design a new reaction from known reaction having close similarity indices.

The most appropriate reaction conditions or the closest performed reaction may be selected from an electronic notebook database.

Various exemplary embodiments of the present invention provide a method for performing chemical testing, for example in screening experiments. The method may comprise performing a plurality of chemical reactions in a plurality of reactors, for example in the wells of a test plate.

For each chemical reaction, the reaction condition may be determined based on the result of a query aimed at sorting the reaction condition for a similar chemical reaction.

A method to pilot an automated synthesis platform may include enabling drawing of a query reaction, selecting at last one appropriate reagent and reaction conditions using the method described above for identifying at least one pair of similar chemical reactions between a plurality of reactions each related to the preparation of at least one product from at least one reagent, performing an automatic control of a robot to launch the query reaction with the at least one appropriate reagent and reaction conditions.

Exemplary embodiments of the invention may comprise inputting a chemical reaction drawn by a user on a user interface, determining at least one similar chemical reaction in case the reaction does not exist in a database, and displaying the at least one similar reaction to the user.

Exemplary embodiments of the invention may provide a computer program product comprising computer instructions recorded on a computer medium for performing any of the methods defined above when running on a computer system.

Exemplary embodiments of the invention also may provide a database search engine to perform any of the methods as defined above to subdivide a large database into a focussed database.

DETAILED DESCRIPTION OF EXEMPLARY EMBODIMENTS

It is to be understood that both the foregoing general description and following detailed description are exemplary and explanatory only and are not restrictive of the invention.

The accompanying figures, which are incorporated in and constitute a part of this specification, illustrate exemplary embodiments and together with the description, serve to explain certain principles.

FIG. 6 shows the .rxn format file of the reaction of FIG. 2;

FIG. 7 is an edition of the CGR of the FIG. 3 in the .mol format;

FIG. 8 is a set of fragment descriptors containing at least one dynamic bond and of length 2 to 6 generated from the query of FIG. 2;

FIG. 14 is a set of fragment descriptors of length 2 to 6 containing at least one dynamic bond generated from the query of FIG. 12

FIG. 15 shows a CGR vector associated with the set of FIG. 14;

FIG. 16 is an exemplary screenshot providing the user with additional information about a chemical function that is not transformed in the query reaction but is detected in the database as a reactive function;

FIG. 17 shows an exemplary table that may be used in the invention to code both for dynamical and conventional bonds.

Figure 1:
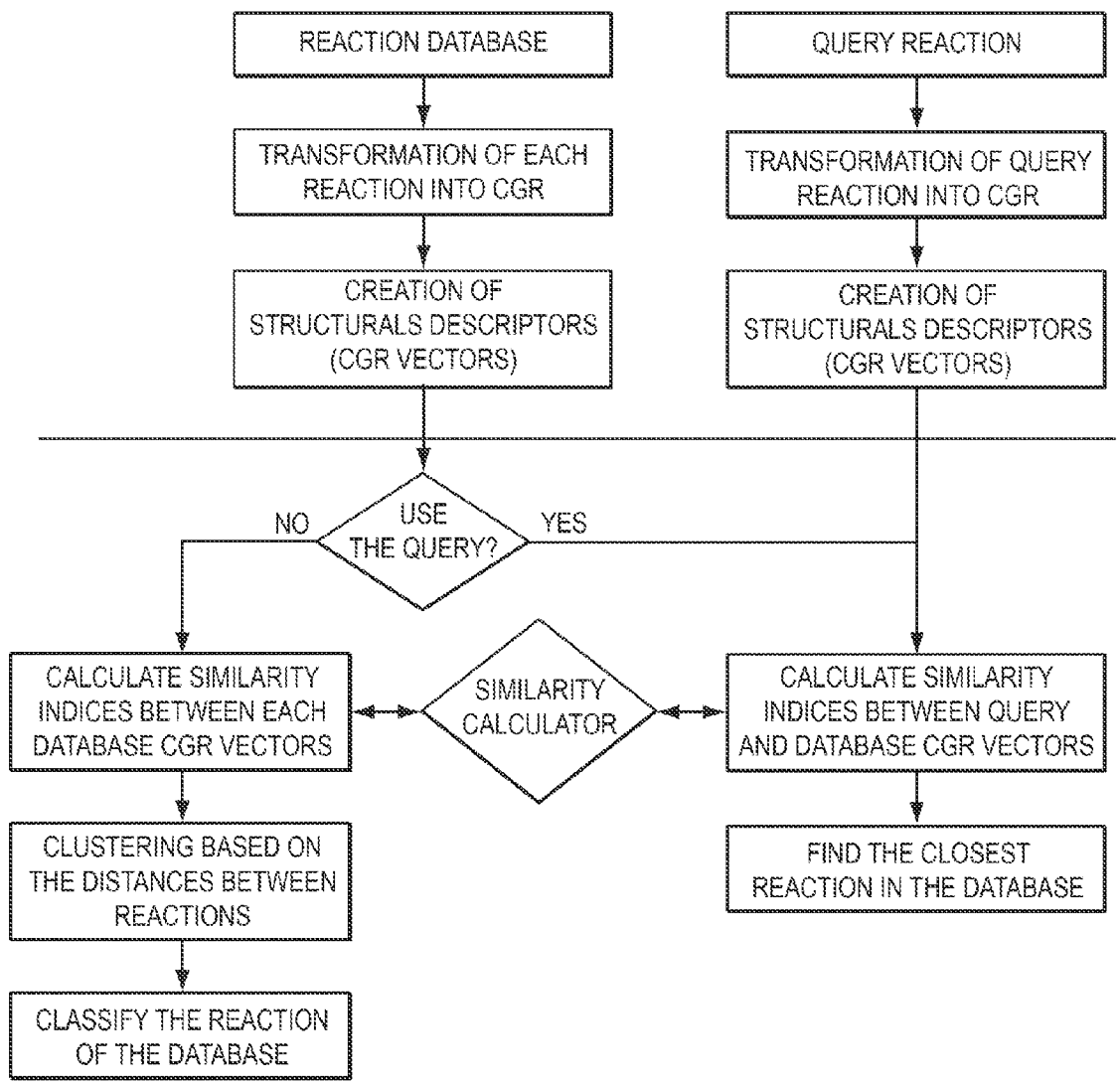
FIG. 1 is a block diagram of methods in accordance with the invention.

In accordance with exemplary aspects of the present teachings, a method may comprise accessing a reaction database, as shown in FIG. 1, in order, for example, to investigate the database and classify a plurality of reactions of the database or to find at least one reaction in the database that is similar to a query reaction. The method may be computer-implemented.

The method may be performed in order to find in the database a reaction similar to a query reaction or to classify reactions in the database. In either case, the method may involve calculating similarity indices between pairs of descriptor vectors using a similarity calculator. The similarity calculator can be implemented by software operating on a computer, such as, for example, a personal computer or a more powerful computer. Alternatively, the similarity calculator may be implemented by software operating on multiple computers which may be linked by a network such as an intranet or Internet.

In an exemplary embodiment, the descriptor vectors comprise database CGR vectors that are generated from a plurality of reactions listed in the database. These database CGR vectors enable calculation of similarity indices either between them when the purpose is to classify the reactions in the database or between a plurality of them, which may then be called candidate CGR vectors, and a CGR query vector when the purpose is to find in the database at least one reaction similar to the query reaction.

The user may submit the reaction query written in any appropriate format by any convenient software. The user may enter the query directly on a computer running software configured to perform the method or indirectly using a web browser by connecting on a convenient website. The query reaction may be drawn by the user.

In an example, the .rxn format described in the *CTFile Format* of October 2003 by the company MDL Information Systems, Inc. California is used, but any other format may be used to describe the query reaction.

The reaction may contain at least one reagent and at least one product and may be mapped and tagged to allow the generation of the CGR. The mapping of the reaction may comprise associating the atoms on the left side of the arrow with the corresponding atoms on the right side of the arrow.

A tagged reaction as used herein may refer to the existence of a fuzzy notification of the dynamical bond as described in the CTFile *Format* of October 2003 by the MDL company.

Figure 2:
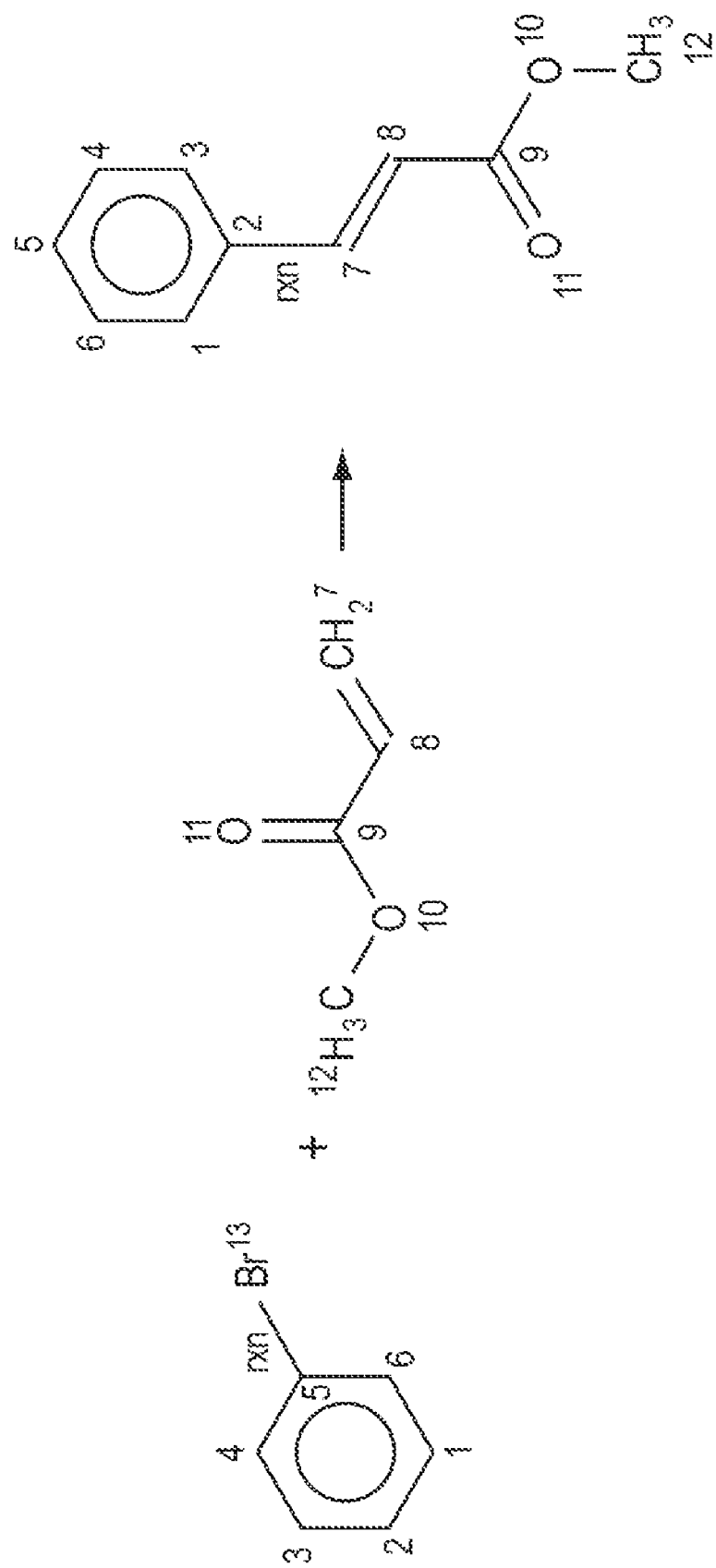
FIG. 2 is an example of query reaction as it may be drawn by a user.

In the example shown in FIG. 2, the reaction involves two reagents and one product. If more than one product is involved in the reaction, the latter may be split into n reactions where n is the number of products.

Figure 3:
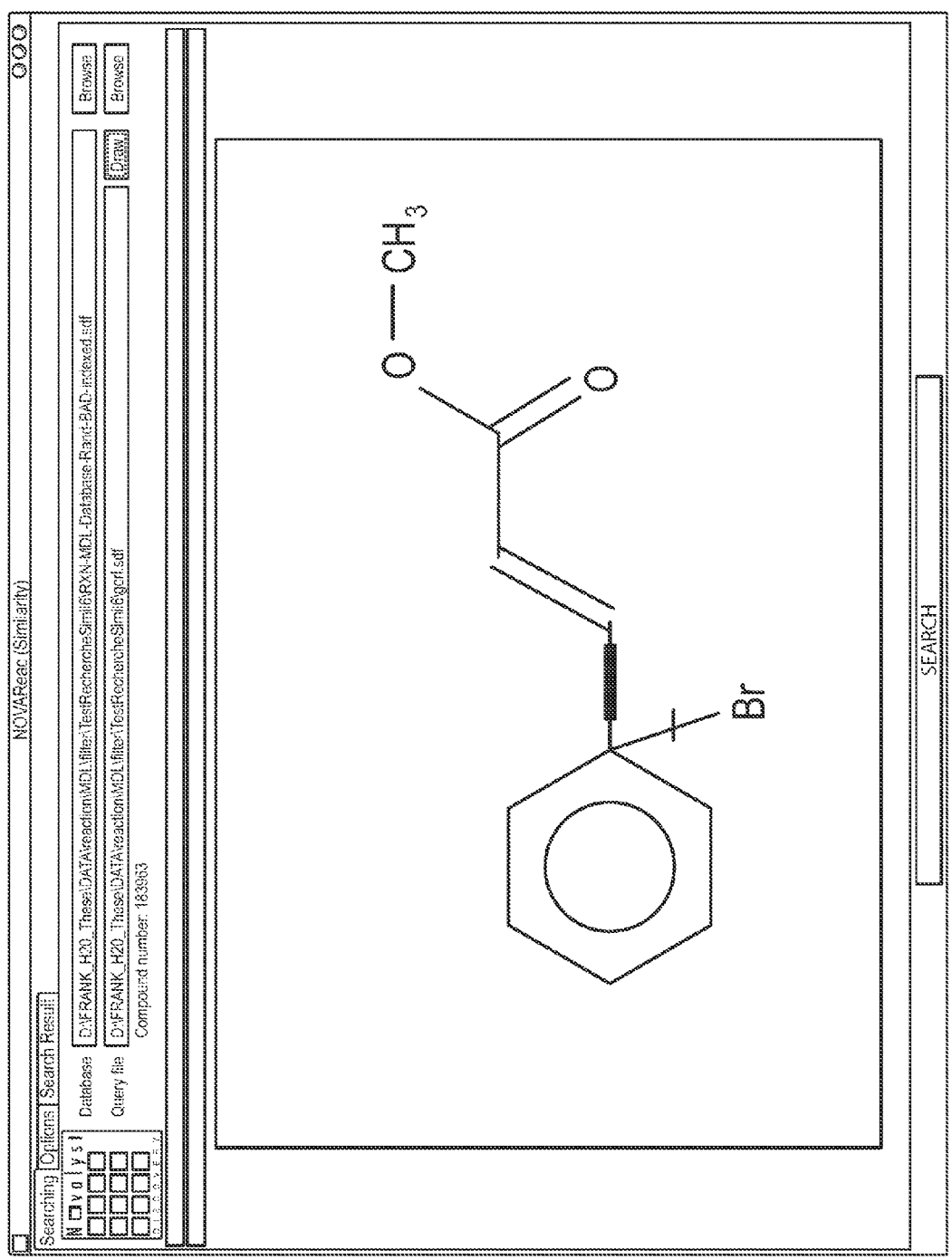
FIG. 3 is a Condensed Graph of Reaction corresponding to the reaction of FIG. 2 as it may be displayed in a graphic interface of a computer system according to an exemplary embodiment of the invention.

Once the query is properly submitted, for example, either via a query reaction or via a reaction database, as in the first steps shown in the flowchart of FIG. 1, a CGR may be generated by transforming the CGR, as illustrated in the second steps of the flowchart of FIG. 1. The CGR may be displayed, as shown in the screen shot of FIG. 3, using the information of the mapping and the tags. If this information is not present, the software may possibly perform automatic mapping. The CGR need not be displayed to perform the method.

FIG. 6 shows the partially edited .rxn file corresponding to the reaction of FIG. 2.

FIG. 7 shows the edited file containing the CGR in the .mol format. Some additional information is added to code for dynamical bonds, for example, in accordance with the table given in FIG. 17. In this example, the lines indicated by the arrows in FIG. 7 indicate 18 as the dynamical bond type, which means according to the table of FIG. 17 that the dynamical bond is a single broken bond.

CGR vectors may be generated both for the query reaction and any reaction listed in the database, as shown in the third steps represented in FIG. 1. The CGR vectors corresponding to the reactions of the database may be generated in advance before the query is made and stored in the database.

Figure 4:
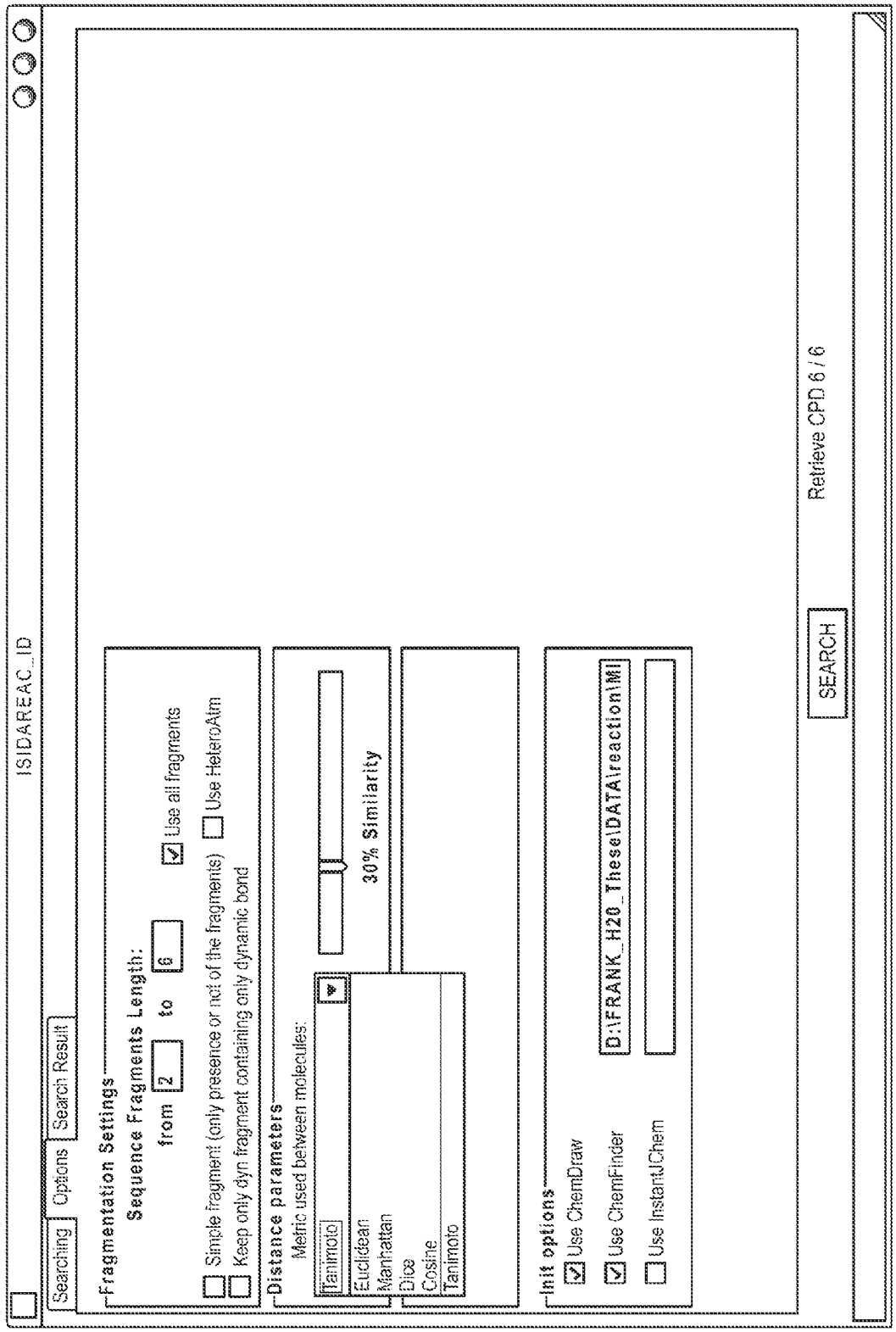
FIG. 4 is an exemplary screenshot (screen capture) illustrating the selection of a metric for computing similarity indices

FIG. 4 shows that the method may comprise prompting the user to select a metric for the similarity calculation and a fragment length, for example a length ranging from 2 to 6.

The metric may comprise at least one of the following distances; Tanimoto coefficients (1), Dice coefficients (2), Cosine Coefficients (3), Euclidean distance (4), Hamming distance (5) or Soergel distance (6), as given by the formula below:

$$T_{QR} = \frac{\sum_{i=1}^{N}(Q_i R_i)}{\sum_{i=1}^{N}(Q_i)^2 + \sum_{i=1}^{N}(R_i)^2 + \sum_{i=1}^{N}(Q_i R_i)} \quad (1)$$

$$D_{QR} = \frac{2\sum_{i=1}^{N}(Q_i R_i)}{\sum_{i=1}^{N}(Q_i)^2 + \sum_{i=1}^{N}(R_i)^2} \quad (2)$$

$$C_{QR} = \frac{\sum_{i=1}^{N}(Q_i R_i)}{\left[\sum_{i=1}^{N}(Q_i)^2 + \sum_{i=1}^{N}(R_i)^2\right]^{\frac{1}{2}}} \quad (3)$$

$$E_{QR} = \left[\sum_{i=1}^{N}(Q_i - R_i)^2\right]^{\frac{1}{2}} \quad (4)$$

$$H_{QR} = \sum_{i=1}^{N}|Q_i - R_i| \quad (5)$$

$$S_{QR} = \frac{\sum_{i=1}^{N}|Q_i - R_i|}{\sum_{i=1}^{N}\max(Q_i - R_i)} \quad (6)$$

$Q_i$ corresponds to the value of the descriptor i associated with the query and $R_i$ corresponds to the value of the descriptor i associated with a candidate reaction of the database. Reference can be made to the article Chemical Similarity Searching, J. Chem. Inf. Comput. Sci. 1998, 38, 983-996 which is hereby incorporated by reference in its entirety, for further details about those distances.

The cut-off value and/or number of results to show may also be set by the user at this stage, as shown in FIG. 4.

The method in accordance with the present invention may be performed using descriptor vectors coding the occurrence of the fragments. In a variant, the method may be performed using descriptor vectors coding only the presence of the fragments.

Figures 9, 10, 12:
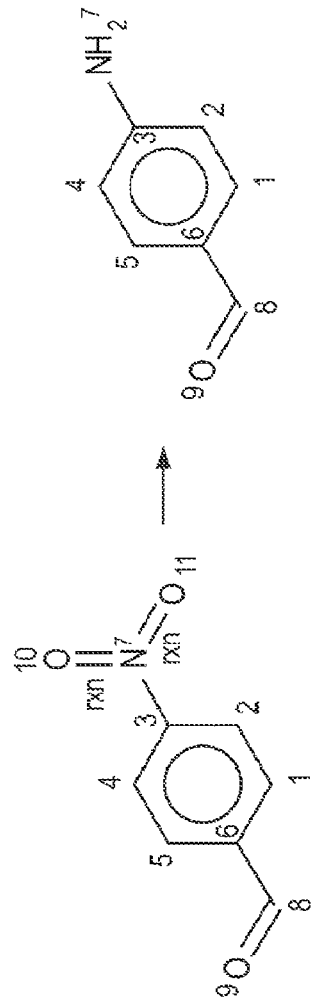
FIG. 9 shows an example of CGR vector associated to the set of FIG. 8, comprising information related to the occurrence of each fragment.
FIG. 10 shows another example of CGR vector associated to the set of FIG. 8, in a bit string form, with only the presence, and not the occurrence, of fragment coded.
FIG. 12 is another example of a query reaction.

A CGR vector may have the format shown in FIG. 9. The CGR vector of FIG. 9 may have for attributes a pair. The first number in the pair of attributes indicates a fragment number in the list of all different fragments generated for the corresponding reaction of predetermined length comprising dynamical bonds. The second number in the pair of attributes indicates the occurrence of that fragment in the set of fragment descriptors generated from the CGR.

For example, in the CGR vector of FIG. 9 a pair of attributes indicates that the fragment #10, i.e. Br5C, which means a broken bond between a brome atom and a carbon atom, is to be found twice in the set of all fragments that may be generated including dynamic bonds with the predetermined length 2 to 6.

FIG. 10 is another example of CGR vector of a bit string type, in which only the presence, and not the occurrence, of a fragment is coded. The file of FIG. 10 may be created by the software performing the method based on the vector of FIG. 9.

Figure 5:
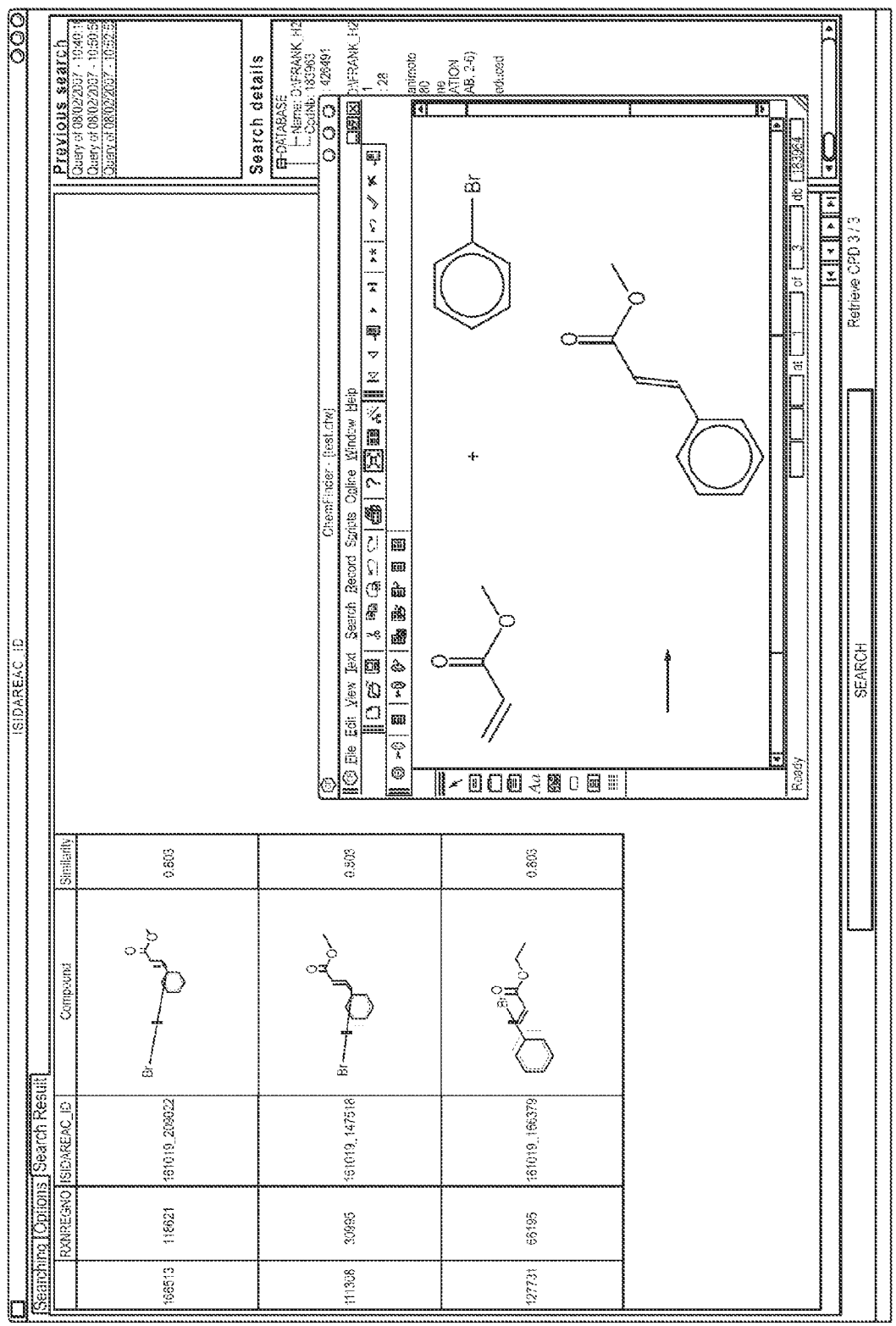
FIG. 5 is an exemplary screenshot showing the results corresponding to the query of FIG. 2 sorted by similarity indices

FIG. 5 is a screenshot showing the results sorted by decreasing similarity indices corresponding to the query of FIG. 2.

The method may allow retrieving reaction information by clicking on a corresponding result, for example by clicking on the compound identification number.

The results displayed may comprise the corresponding CGRs as shown in FIG. 5.

Figure 13:
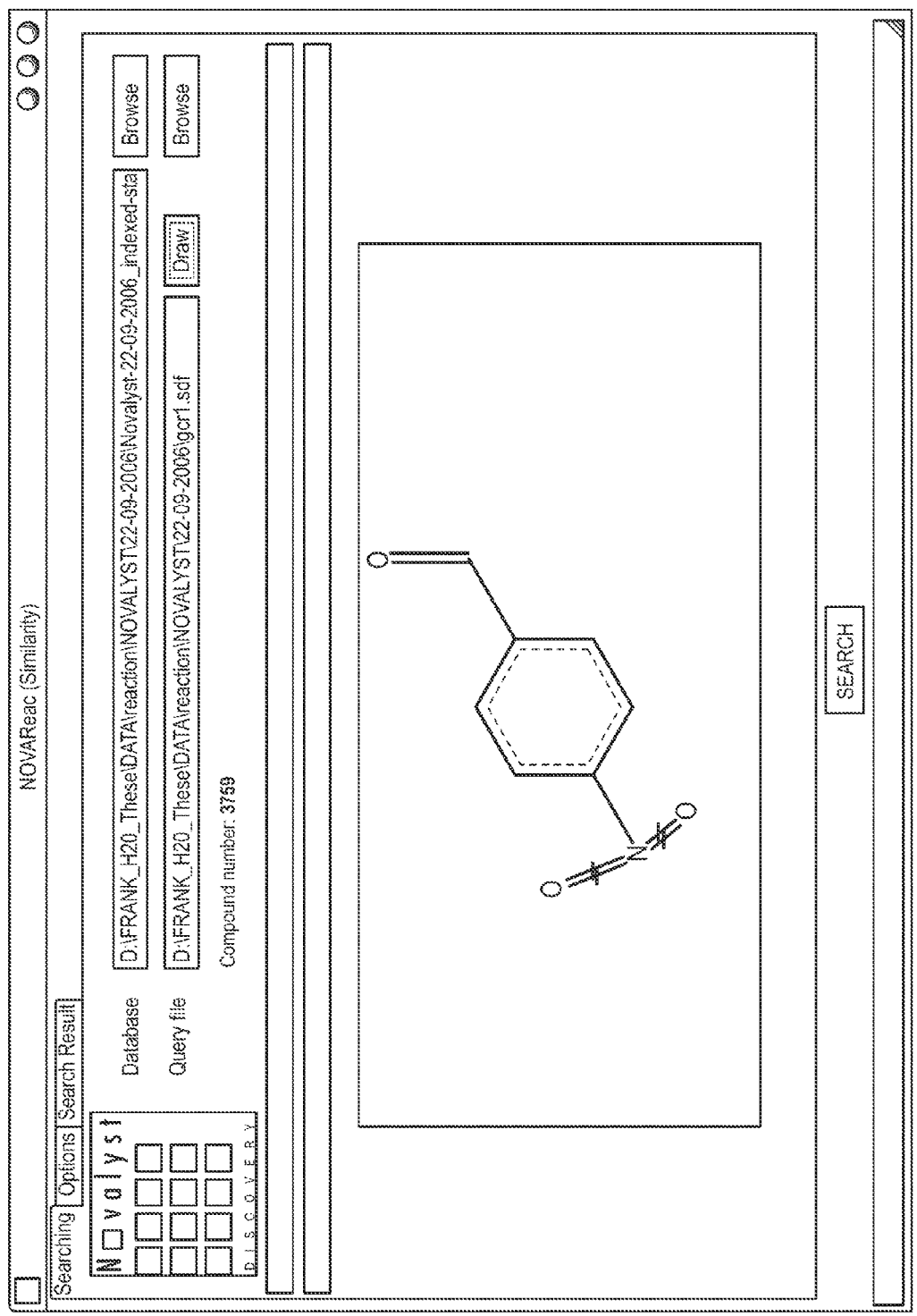
FIG. 13 is an exemplary screenshot showing the CGR corresponding to the query of FIG. 12.

FIGS. 12 and 13 illustrate another example of a query reaction. The set of fragment descriptors containing at least one dynamic bond and of length 2 to 6 for this query and the corresponding descriptor vector are shown respectively in FIGS. 14 and 15.

The invention may provide the user with additional information relative to the query to inform the user when a chemical function that did not react in the query reaction may react under some reaction conditions.

To provide the user with this additional information, a list of fragments may be generated listing all the fragments before modification and the corresponding fragment containing at least one dynamical bond. All the transformations occurring in the database may be listed in such a file.

Figure 11:
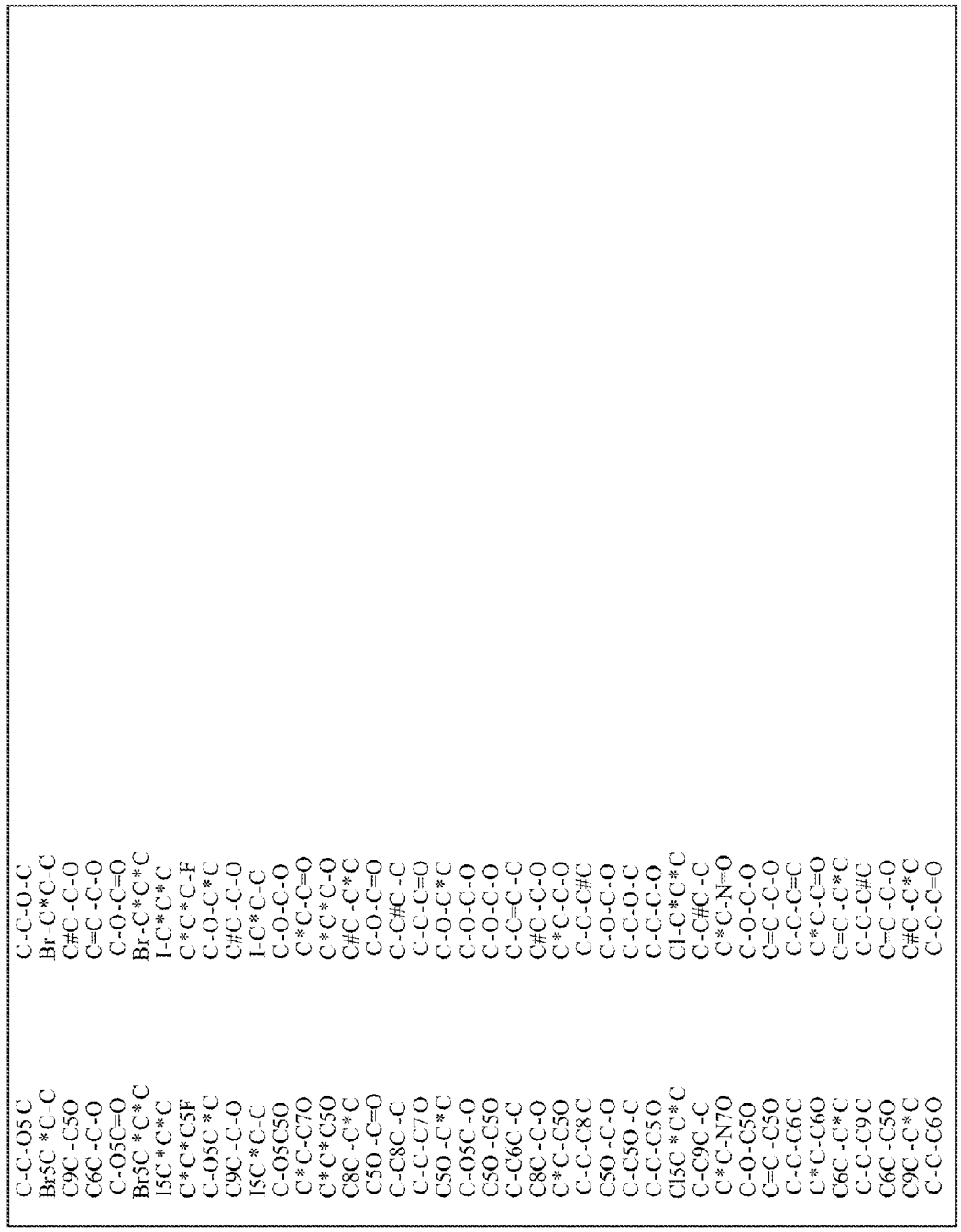
FIG. 11 is a list extracted from the database of fragments of length 4 indicating changes to the fragments

FIG. 11 shows an example of such a dual list of transformation of fragments of 4 atoms. The right column shows the fragments before modification and the left column shows the fragments containing at least one dynamical bond. A list similar to FIG. 11 may also be generated for the query and the fragments of left columns of these two lists may be compared. If some matching is found, this means that a matching fragment that may experience a transformation has been found in the query.

The right column of the list may be used to perform a substructural search in the database to find all the reactions that contain these right column fragments. By crossing the reaction conditions of the reaction sorted by the substructural search with the reaction condition corresponding to the query, chemical reactions involving a transformation of a same fragment may be released to the user, for example by being displayed on a screen, as shown in FIG. 16.

Figure 16:
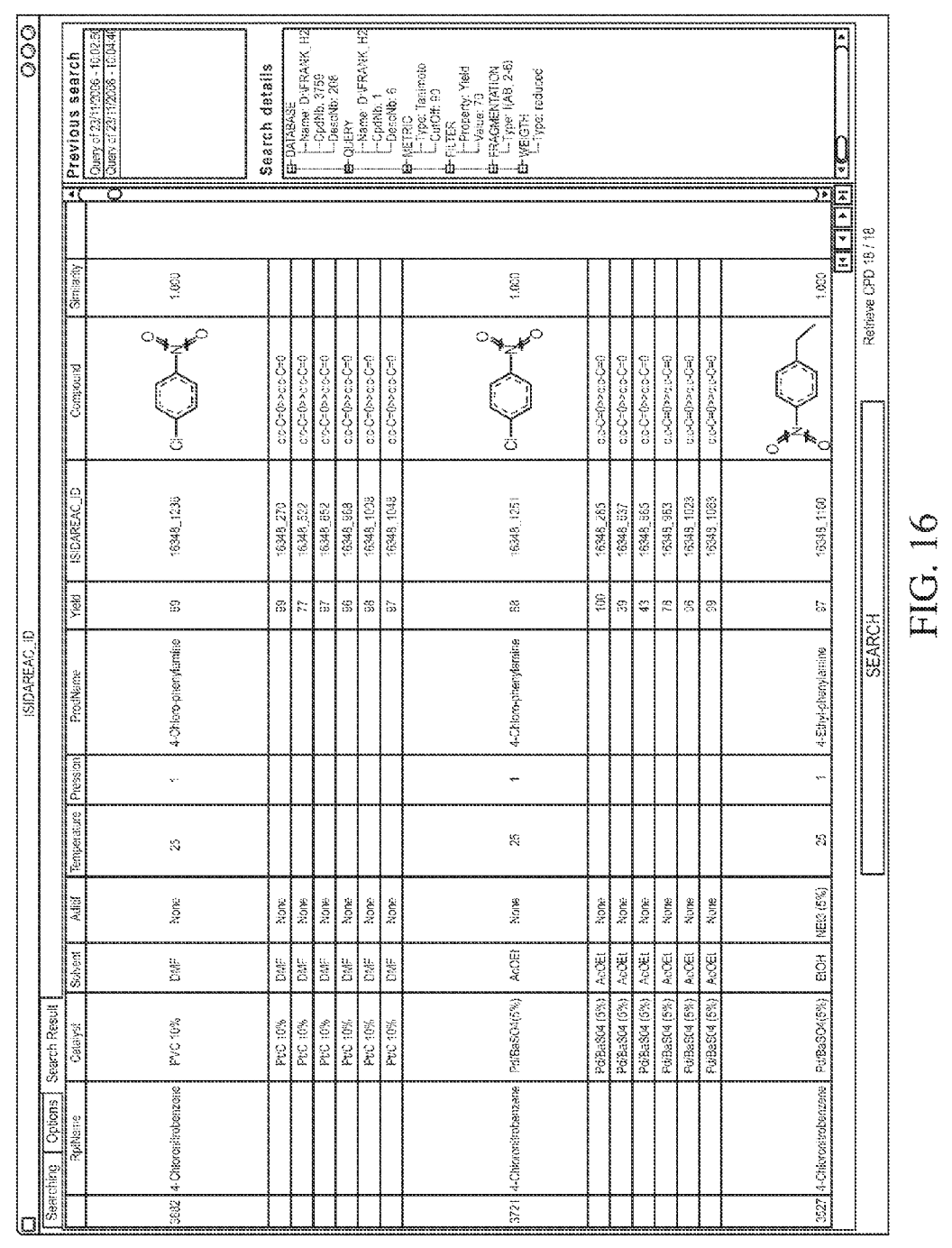

FIG. 16 is a screenshot on which two CGRs similar to the CGR resulting from the query of FIG. 12 are displayed involving a possible transformation of the function c:c-c=0. The yield of the non-transformation of the fragment is displayed, which means that the lower the yield is, the more the fragment is transformed. A cut-off value of, for example, 70% may be selected and the results may be displayed in different colors depending on whether the yield is over or under this cut-off value.

The lines in dark grey, corresponding to reactions with yields of 39 and 43, indicate that in the same reaction condition, the function ci c:c-C=O is also transformed.

In the example shown, the reaction conditions involving Pt/C 10% as a catalyst do not lead to significant transformation of fragment c:c=0 while the choice of Pd/BaSO$_4$ (5%) as a catalyst may lead for some reactions to a significant transformation of c:c=0.

The lines in light grey in this example indicate that the function is not transformed. If all the lines are light grey, this indicates that the reaction conditions are likely to be appropriate for performing the query reaction.

Various exemplary embodiments of the invention may prove useful for screening of chemical reactions.

The screening may comprise using a pipette to supply wells of a testing plate with at least two compounds intended to react.

Each reaction that is tested may be initiated and tested by a robot operating under a computer system. This computer system may send a query to a different computer system performing the method described above for sorting similar chemical reactions or the same computer system may execute software implementing such a method. Based on the results of the query, the reaction conditions under which the reaction is tested may be set automatically so as to correspond to the reaction conditions given for the most similar chemical reaction, and the robot may introduce in the well any substance in accordance with the reaction condition, such as a selected catalyst, for example. Performing the testing under possibly more appropriate reaction conditions may improve significantly the performance of the screening.

Figure 18:
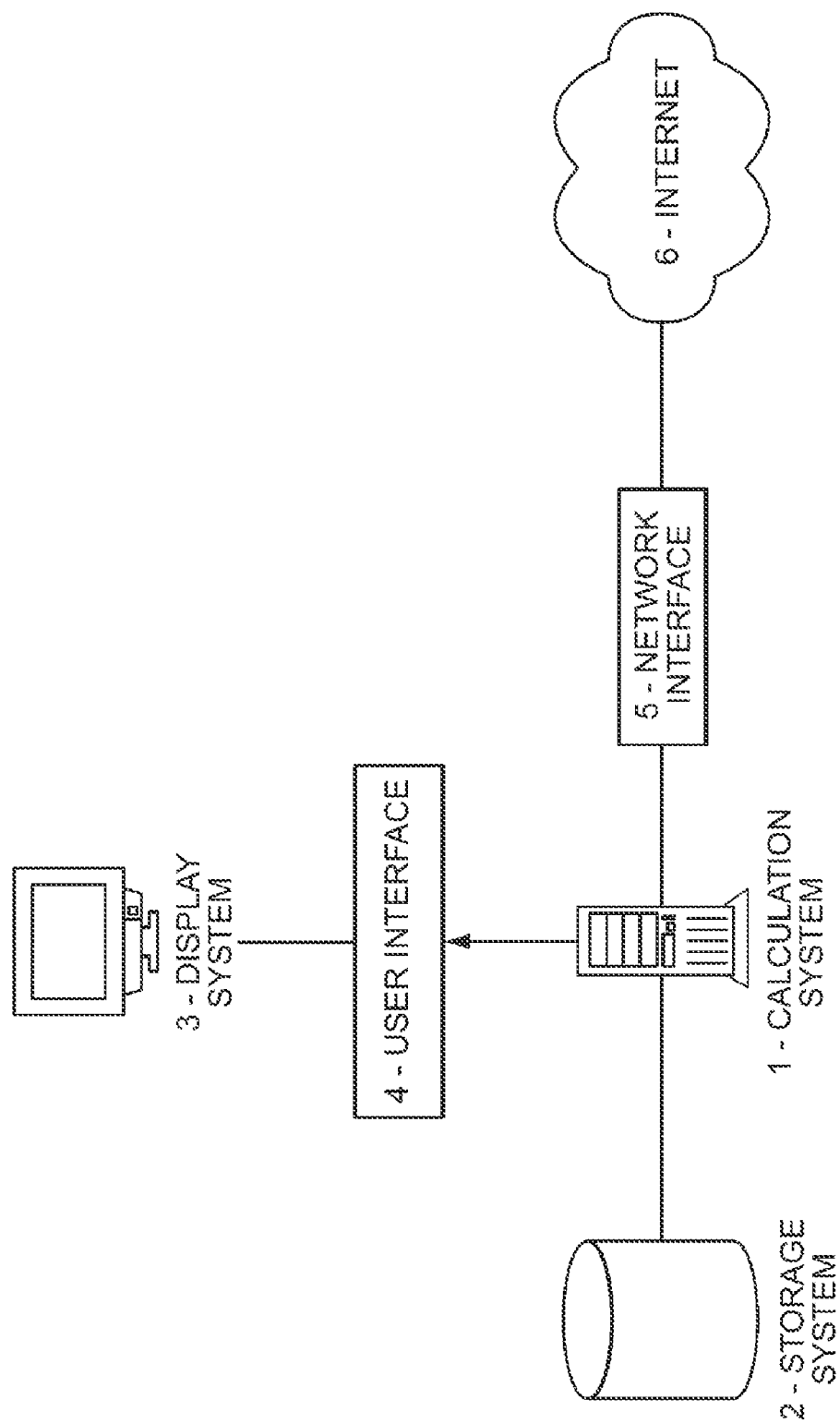
FIG. 18 shows an exemplary computer system for implementing a method in accordance with the present teachings.

In various embodiments, the methods may be performed in any computer system, for example. As shown in FIG. 18, a computer system may comprise a calculation system 1 which may comprise at least one of any known microcomputer or personal computer or more powerful computer comprising one or more processors. The data may be stored on a local computer or on a dedicated server.

The computer system may comprise a storage system that may be internal or external. The storage system 2 may comprise any mass memory, for example optical disk, magnetic tape, hard drive or memory chips, for example flash memory.

The computer system may also comprise a display system 3 comprising, for example, an LCD display, an OLED display, a plasma display, or a CRT display.

The computer system may comprise a user interface 4 which may comprise a keyboard, mouse, sensitive screen, and/or digitizing tablet and/or any other known user interface.

The computer system may comprise a network interface 5 which may comprise any interface configured for enabling exchange of information between the calculation system 1 and any other terminal or server connected to a network 6, such as, for example, an Intranet or Internet.

The method may be performed locally or at least partially remotely by connecting to a website or an intranet site, for example.

The invention is not limited to the embodiments described above. Other embodiments of the invention will be apparent to those skilled in the art from consideration of the specification and practice of the invention disclosed herein. It is intended that the specification and examples be considered as exemplary only.

What is claimed is:

1. A computer based method for identifying at least one pair of similar chemical reactions between a plurality of reactions each related to preparation of at least one product from at least one reagent, the method comprising:
    generating for each reaction a structural representation involving dynamic and conventional bonds;
    generating based on the structural representation, for each reaction, a set of fragment descriptors of a predetermined length comprising the dynamic bonds and a corresponding descriptor vector;
    calculating similarity indices between descriptor vectors of the plurality of reactions;
    comparing the similarity indices to identify at least one pair of similar reactions;
    generating for a query reaction a structural representation involving dynamic and conventional bonds;
    generating based on the structural representation generated for the query reaction a query descriptor vector;
    calculating similarity indices between the query descriptor vector and other descriptor vectors corresponding to reactions listed in a database; and
    comparing the similarity indices between the query descriptor vector and other descriptor vectors to identify at least one reaction similar to the query reaction in the database.

2. The method of claim 1, further comprising retrieving reaction condition information related to the at least one pair of similar reactions.

3. The method of claim 1, further comprising classifying reactions listed in a database according to the similarity indices calculated for each pair of reactions in the database.

4. The method of claim 1, wherein the descriptor vector comprises a CGR vector.

5. The method of claim 4, wherein the CGR vector for each reaction comprises attributes representative of a number of occurrences of corresponding fragment descriptors in the set of fragment descriptors.

6. The method of claim 4, wherein the CGR vector for each reaction comprises attributes representative of the presence of corresponding fragment descriptors in the set of fragment descriptors.

7. The method of claim 1, wherein calculating similarity indices comprises calculating a distance selected from one of Hamming distance, Euclidean distance, Soergel distance, Tanimato coefficients, Dine coefficients and Cosine coefficients.

8. The method of claim 1, wherein comparing the similarity indices comprises comparing the similarity indices to a cut-off value.

9. The method of claim 8, further comprising enabling a user to select the cut-off value.

10. The method of claim 1, further comprising identifying in the query fragments which are transformed according to the information in the database and that are not transformed in the query.

11. A computer program product comprising computer instructions recorded on a computer medium for performing the method of claim 1 when running on a computer system.

12. A database search engine performing the method of claim 1 to subdivide a large database into a focussed database.

13. A method to pilot an automated synthesis platform, the method comprising:
    enabling drawing of a query reaction;
    selecting at last one appropriate reagent and reaction condition using the method of claim 1; and
    performing an automatic control of a robot to launch the query reaction with the at least one appropriate reagent and reaction condition.

14. A method for performing chemical testing, the method comprising:
    performing a plurality of chemical reactions in a plurality of reactors, wherein for each chemical reaction, the reaction condition is determined by implementing the method of claim 1 based on the result of a query aimed at sorting the reaction condition for a similar chemical reaction.

* * * * *